United States Patent
Tsien et al.

(10) Patent No.: US 6,608,671 B2
(45) Date of Patent: *Aug. 19, 2003

(54) DETECTOR AND SCREENING DEVICE FOR ION CHANNELS

(75) Inventors: Roger Y. Tsien, La Jolla, CA (US); Peter J. Coassin, Encinitas, CA (US); Andrew A. Pham, Del Mar, CA (US); Alec Tate Harootunian, Del Mar, CA (US); Minh Vuong, San Diego, CA (US)

(73) Assignee: Vertex Pharmaceuticals (San Diego) LLC, San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/118,728

(22) Filed: Jul. 17, 1998

(65) Prior Publication Data

US 2002/0001075 A1 Jan. 3, 2002

(51) Int. Cl.⁷ .................... G01N 21/00; G01N 21/64; G01N 21/66
(52) U.S. Cl. .................... 356/72; 356/436; 356/440; 422/82.08
(58) Field of Search .................... 422/82.05, 82.08, 422/82.09; 356/434, 440, 72; 385/12, 13

(56) References Cited

U.S. PATENT DOCUMENTS

| | | | |
|---|---|---|---|
| 3,885,879 A | | 5/1975 | Louder et al. |
| 3,905,852 A | | 9/1975 | Mukai et al. |
| 4,204,743 A | | 5/1980 | Etaix |
| 4,225,230 A | * | 9/1980 | Dostoomian et al. ....... 356/407 |
| 4,265,511 A | | 5/1981 | Nicia et al. |
| 4,630,923 A | | 12/1986 | Tans et al. |
| 4,714,345 A | | 12/1987 | Schrader |
| 4,737,464 A | | 4/1988 | McConnell et al. |
| 4,747,687 A | | 5/1988 | Hoppe et al. |
| 4,759,601 A | | 7/1988 | Knutsen et al. |
| 4,792,689 A | | 12/1988 | Peterson |
| 4,800,164 A | | 1/1989 | Bisconte |
| 4,922,092 A | | 5/1990 | Rushbrooke et al. |
| 5,026,139 A | | 6/1991 | Klainer et al. |
| 5,034,189 A | | 7/1991 | Cox et al. |
| 5,037,199 A | | 8/1991 | Hlousek |
| 5,086,220 A | | 2/1992 | Berthold et al. |
| 5,096,671 A | | 3/1992 | Kane et al. |
| 5,138,153 A | | 8/1992 | Gergely et al. |
| 5,168,156 A | * | 12/1992 | Fischer et al. ............... 356/436 |
| 5,216,488 A | * | 6/1993 | Tguunanen et al. ........ 356/440 |
| 5,217,285 A | | 6/1993 | Sopori |
| 5,239,360 A | | 8/1993 | Moring et al. |
| 5,244,636 A | | 9/1993 | Walt et al. |
| 5,250,264 A | | 10/1993 | Walt et al. |
| 5,252,494 A | | 10/1993 | Walt |
| 5,280,389 A | | 1/1994 | Kunikane et al. |
| 5,283,178 A | | 2/1994 | Kessler et al. |
| 5,298,741 A | | 3/1994 | Wakt et al. |
| 5,307,144 A | * | 4/1994 | Hiroshi et al. ............... 356/440 |

(List continued on next page.)

FOREIGN PATENT DOCUMENTS

| | | |
|---|---|---|
| DE | 3036638 | 4/1982 |
| EP | 023679 A | 8/1987 |
| EP | 0521636 A1 | 1/1993 |

(List continued on next page.)

OTHER PUBLICATIONS

"FLIPR", Molecular Devices Corp. 1997.

Primary Examiner—Zandra U Smith
(74) Attorney, Agent, or Firm—Gray Cary Ware & Freidenrich, LLP

(57) ABSTRACT

The invention provides for a detector assembly, fiber assembly and screening system for optical measurements.

40 Claims, 9 Drawing Sheets

U.S. PATENT DOCUMENTS

| | | |
|---|---|---|
| 5,311,611 A | 5/1994 | Migliaccio |
| 5,320,814 A | 6/1994 | Walt et al. |
| 5,347,122 A | 9/1994 | Ansorge et al. |
| 5,371,600 A | 12/1994 | Hsia et al. |
| 5,399,866 A | 3/1995 | Feldman et al. |
| 5,436,718 A | 7/1995 | Fernandes et al. |
| 5,498,549 A | 3/1996 | Nagel et al. |
| 5,557,398 A | 9/1996 | Wechsler et al. |
| 5,569,911 A | 10/1996 | Tomlinson, Jr. et al. |
| 5,589,351 A | 12/1996 | Harootunian |
| 5,627,638 A | 5/1997 | Vokhmin |
| 5,636,017 A | 6/1997 | Bruno et al. |
| 5,638,475 A | 6/1997 | Gaebe |
| 5,670,113 A * | 9/1997 | Akong et al. ............... 356/414 |
| 5,672,515 A | 9/1997 | Furlong |
| 5,678,751 A | 10/1997 | Buchanan et al. |
| 5,684,711 A | 11/1997 | Agrafiotis et al. |
| 5,689,354 A | 11/1997 | Orino |
| 5,694,215 A | 12/1997 | Carver |
| 5,714,388 A | 2/1998 | Kusnetz |
| 5,745,620 A | 4/1998 | Bergmann |
| 5,763,277 A | 6/1998 | Zhu et al. |
| 5,769,791 A | 6/1998 | Benaron et al. |
| 5,774,610 A | 6/1998 | O'Rourke et al. |
| 5,837,196 A | 11/1998 | Pinkel et al. |
| 5,926,592 A * | 7/1999 | Harris et al. ................ 385/127 |
| 5,985,214 A * | 11/1999 | Stylli et al. .................. 422/65 |

FOREIGN PATENT DOCUMENTS

| | | |
|---|---|---|
| EP | 0 587 281 A2 | 3/1994 |
| EP | 0 590 145 B1 | 4/1994 |
| EP | 0 830 852 | 3/1998 |
| EP | 0 851 230 A2 | 7/1998 |
| FR | 2661986 A | 11/1991 |
| WO | WO 95/00832 | 1/1995 |
| WO | WO 96/02824 A1 | 2/1996 |
| WO | WO 97/10494 | 3/1997 |
| WO | WO 97/26539 | 7/1997 |
| WO | WO 98/09154 | 3/1998 |

\* cited by examiner

Assembly 1

Assembly 2

Assembly 3

Assembly 4

DETECTOR AND SCREENING DEVICE FOR ION CHANNELS

FIELD OF THE INVENTION

The present invention generally relates to devices and methods for rapidly identifying chemicals with biological activity in liquid samples, particularly automated screening of low volume samples for new medicines, agrochemicals, or cosmetics.

BACKGROUND

Drug discovery is a highly time dependent and critical process in which significant improvements in methodology can dramatically improve the pace at which a useful chemical becomes a validated lead, and ultimately forms the basis for the development of a drug. In many cases the eventual value of a useful drug is set by the timing of its arrival into the market place, and the length of time the drug enjoys as an exclusive treatment for a specific ailment.

A major challenge for major pharmaceutical companies is to improve the speed and efficiency of this process while at the same time maintaining costs to an absolute minimum. One solution to this problem has been to develop high throughput screening systems that enable the rapid analysis of many thousands of chemical compounds per 24 hours. To reduce the otherwise prohibitive costs of screening such large numbers of compounds, typically these systems use miniaturized assay systems that dramatically reduce reagent costs, and improve productivity. To efficiently handle large numbers of miniaturized assays it is necessary to implement automatic robotically controlled analysis systems that can provide reliable reagent addition and manipulations. Preferably these systems and the invention herein are capable of interacting in a coordinated fashion with other systems sub-components, such as the central compound store to enable rapid and efficient processing of samples.

Miniaturized high throughput screening systems require robust, reliable and reproducible methods of analysis that are sensitive enough to work with small sample sizes. While there are a large number of potential analysis methods that can successfully used in macroscopic analysis, many of these procedures are not easily miniaturizable, or lack sufficient sensitivity when miniaturized. This is typically true because absolute signal intensity from a given sample decreases as a function of the size of the sample, whereas background optical or detector noise remains more or less constant for large or small samples. Preferred assays for miniaturized high throughput screening assays have a high signal to noise ratios at very low sample sizes.

Fluorescence based measurements have high sensitivity and perform well with small samples, where factors such as inner filtering of excitation and emission light are reduced. Fluorescence therefore exhibit good signal to noise ratios even with small sample sizes. A particularly preferred method of using fluorescence based signal detection is to generate a fluorescent (emission) signal that simultaneously changes at two or more wavelengths. A ratio can be calculated based on the emission light intensity at the first wavelength divided by the emitted light intensity at a second wavelength. This use of this ratio to measure a fluorescent assay has several important advantages over other non-ratiometric types of analysis. Firstly the ratio is largely independent on the actual concentration of the fluorescent dye that is emitting fluorescence. Secondly the ratio is largely independent on the intensity of light with which the fluorescent compound is being excited. Thirdly the ratio is largely independent of changes in the sensitivity of the detector, provided that is that these changes are the same for the detection efficiency at both wavelengths. This combination of advantages make fluorescence based ratiometric assays highly attractive for high throughput screening systems, where day to day, and, assay to assay reproducibility are important.

Fluorescence assays that produce ratiometric emission readouts have gained in popularity as the advantages of the method have grown in acceptance. Changes in emission ratios at two more wavelengths can be created through a number of distinct mechanisms including electronic and conformational changes in a fluorescence compound. Typically, these changes can occur in response to a chemical reaction or binding of the fluorescent compound to a particular ion such as a metal ion like calcium or magnesium, or through a change in pH that influences the protonation state of the fluorescent compound.

Alternatively ratiometric changes in emission can be conveniently be obtained by exploiting the use of fluorescence resonance energy transfer (FRET) from one fluorescent species to another fluorescent species. This approach is predictable, sensitive and can give rise to large ratio changes at two well-defined and well spectrally resolved wavelengths. Furthermore FRET can be generally applied to create ratiometric assays for a range of activities. For example patent WO 96/30540 (Tsien) describes a FRET based system to measure gene expression using a fluorogenic substrate of beta lactamase. Patent WO 96/41166 (Tsien) describes the use of a FRET based system to measure voltage across the plasma membrane of a cell. Patent WO 97/20261 (Tsien) describes the use of FRET between two fluorescent proteins to measure intracellular protein. Such assays can be used with the inventions described herein.

The present invention is directed towards the development of improved optical systems for simultaneously measuring emission ratios from a plurality of samples with high sensitivity, speed, reproducibility and accuracy. The present invention has several important advantages over prior devices adapted to measure fluorescence emission sequentially from samples.

Firstly, the simultaneous measurement of emission ratios enables rapid fluctuations in lamp intensity, bleaching of the fluorescent dye, or cycle to cycle errors in the alignment of multiwell plates to be corrected for, thereby enabling much smaller changes in ratio to be reliably observed. Secondly, no mechanical movements are necessary during ratio measurement, eliminating mechanical design challenges. Thirdly ratios can be acquired very rapidly, as required for dynamic measurements of membrane potential or calcium, and are not limited by the speed of filter changing. Fourthly the overall throughput and duty cycle are improved by eliminating dead times for filter changeover. Finally, residual ratio non-uniformities between addressable wells should be constant and easily correctable by using emission ratios previously measured on reference samples to normalize sample ratios in software.

SUMMARY OF THE INVENTION

The invention includes a method of simultaneously measuring at least two optical properties of emitted light from at least one sample in a plurality of addressable wells of a multiwell plate comprising the steps of, i) aligning a plurality of addressable wells of a multiwell plate to a plurality of ball lenses;

ii) directing electromagnetic radiation substantially coaxially through the symmetry axis of each of said plurality of ball lenses, iii) detecting the emitted light focused by said plurality of ball lenses from said at least one sample.

The invention includes an optical detection system, comprising a light source that launches at least one predetermined wavelength of light, sample holder, a ball lens at a predetermined interrogation distance from said sample holder, a trifurcated fiber adapted for dual optical interrogation and in optical communication with said ball lens, and a detector that detects light of at least one desired wavelength and in optical communication with said ball lens. Typically, the optical detection system includes a trifurcated fiber comprising a first plurality of emission bundles for receiving light of a first wavelength and second plurality of emission bundles for receiving light of a second wavelength and said first plurality of emission bundles and said light source launches at least one predetermined wavelength of excitation light at said sample holder. The optical detection system may further comprise at least one positioner to controllably change the spatial relationship between the ball lens and the fiber or sample or a combination thereof. Typically, the light source launches light through said trifurcated fiber to the location at least one addressable well in a sample in said sample holder to monitor epifluorescence. Preferably, the trifurcated fiber comprises an end that is generally at a focal plane of the ball lens.

The invention also includes an optical fiber assembly, comprising a trifurcated fiber comprising a first plurality of emission bundles for receiving light of a first wavelength and second plurality of emission bundles for receiving light of a second wavelength and said first plurality of emission bundles and said second plurality of emission bundles are non-randomly distributed in plurality of excitation bundles.

DETAILED DESCRIPTION OF THE INVENTION

Definitions

Figure 1:
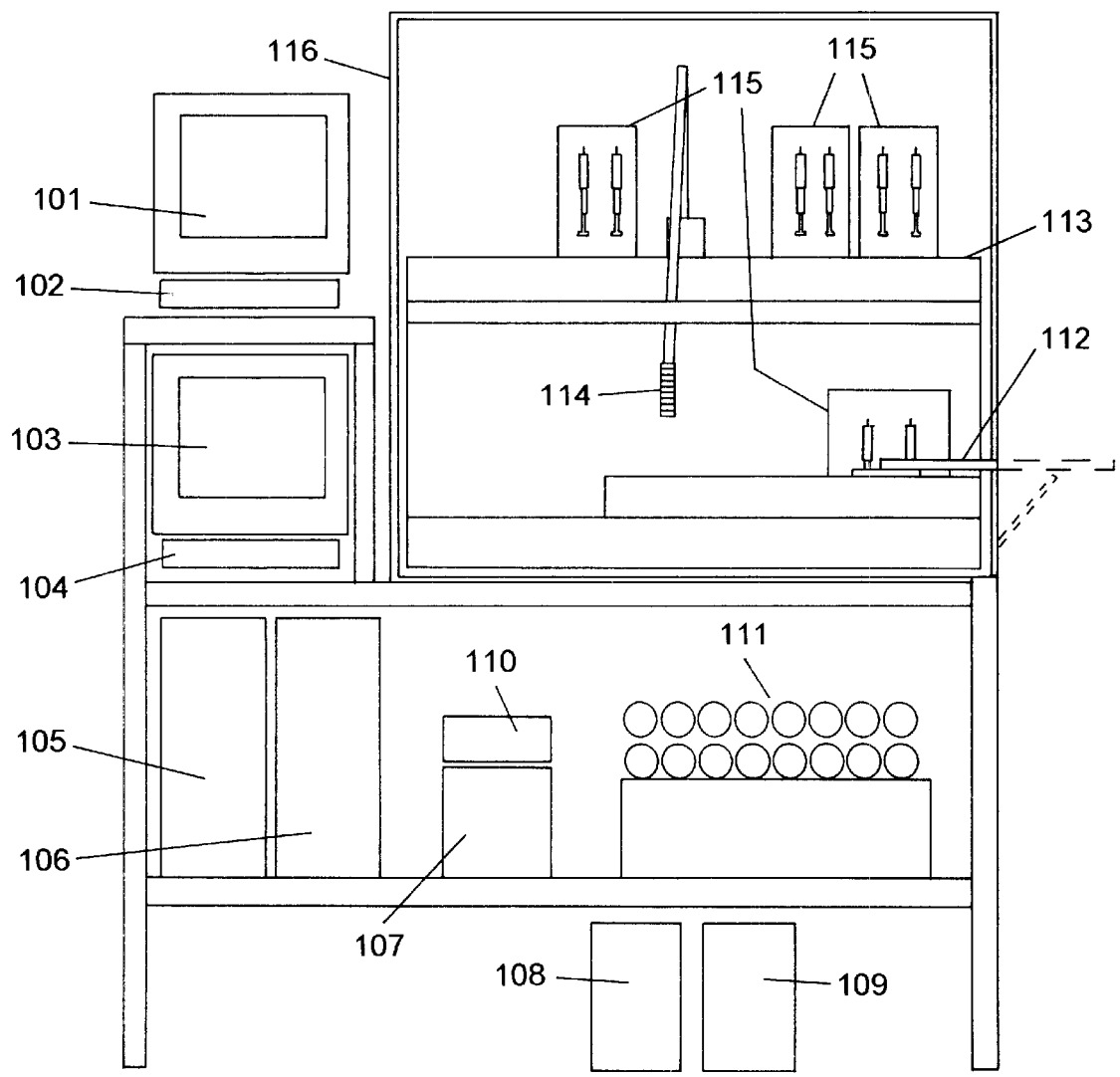
FIG. 1 shows one embodiment of a fluorescence measuring device utilizing the detection system of the invention.

Unless otherwise defined, all technical and scientific terms used herein have the same meaning as commonly understood by one of ordinary skill in the art to which the invention belongs. Generally, the nomenclature used herein and many of the automation, computer, detection, chemistry and laboratory procedures described below are those well known and commonly employed in the art. Standard techniques are usually used for engineering, robotics, optics, molecular biology, computer software and integration. Generally, chemical reactions, cell assays and enzymatic reactions are performed according to the manufacture's specifications where appropriate. The techniques and procedures are generally performed according to conventional methods in the art and various general references (see generally Lakowicz, J. R. *Principles of fluorescence spectroscopy*, New York: Plenum press (1983), and Lakowicz, J. R. *Emerging applications of fluorescence spectroscopy to cellular imaging: lifetime imaging, metal-ligand probes, multi-photon excitation and light quenching*. Scanning Microsc Suppl VOL. 10 (1996) pages. 213–24, for fluorescent techniques, Sambrook et al *Molecular Cloning: A laboratory manual*, $2^{nd}$ ed. (1989) Cold Spring Harbor Laboratory Press, Cold Spring Harbor, N.Y. for molecular biology methods, Optics Guide 5 Melles Griot® Irvine, Calif. for general optical methods, Optical Waveguide Theory, Snyder & Love published by Chapman & Hall, and Fiber Optics Devices and Systems by Peter Cheo, published by Prentice-Hall for fiber optic theory and materials.

As employed throughout the disclosure, the following terms, unless otherwise indicated, shall be understood to have the following meanings:

"Multiwell plate" refers to a two dimensional array of addressable wells located on a substantially flat surface. Multiwell plates may comprise any number of discrete addressable wells, and comprise addressable wells of any width or depth. Common examples of multiwell plates include 96 well plates, 384 well plates and 3456 well nanoplates.

"Addressable well" refers to spatially distinct location on a multiwell plate that may or may not have a physical representation outside of the computer representation of the plate.

"Chemical plate" refers to a multiwell plate containing chemicals, such as stock solutions or dilutions thereof.

"Pharmaceutical agent or drug" refers to a chemical compound or composition capable of inducing a desired therapeutic effect when properly administered to a patient.

As used herein, "optical property" refers a measurable property of light, such as the intensity of emission light at a particular wavelength, the intensity or degree of light polarization, the transmittance of a compound or composition, or the reflectance of a compound or composition.

"Ball lens" refers to a sphere, truncated sphere, cylinder, or truncated cylinder of suitable transparent refractive material and is usually a sphere.

"Operably linked" refers to a juxtaposition wherein the components so described are in a relationship permitting them to function in their intended manner.

Description of One Embodiment of the Invention

FIG. 1 shows one device of the invention. In one embodiment of the invention, a device integrates a liquid handler 115, a multiwell positioning stage 112 and a detection device comprising the ball lens trifurcated plates containing cells and compounds are loaded into the device either manually or by a robotic system. The device then takes the plate(s) into the light-tight reading area 116. The equipment may include a liquid handler 115 (such as a modified Hamilton Micro Lab 2200 MPH, Hamilton Co, Reno, Nev.), and at least 1 dispensing tip 114, a multi-well plate positioning stage (500000 series, Parker Hannifin Corp, Harrison City, Pa.), in addition to the device of the invention. Basal fluorescence readings are made at both emission wavelengths prior to compound addition.

In one embodiment the system was designed to simultaneously measure fluorescence at two different emission wavelengths from a column of 8 wells before, during, and after the introduction of a fluid sample obtained from another multiwell plate or trough.

A compound or compounds are then added to the cells while fluorescence at both emission wavelengths is continuously measured. After the whole plate is read, it is moved out of the light-tight enclosure and retrieved by the manual user or robotic system.

16 photomultipliers are used to detect fluorescence emission at a rate of 1 Hz or 10 Hz. Both excuation and emission wavelengths are selected via interference filters. The 300 W xenon arc lamp provides illumination from 350 nm to 650 nm. The multi-alkali photomultiplier (Hamamatsu HC124-01) tubes can detect wavelengths ranging from 300 to 850 nm. The bi-alkali photomultiplier tubes can detect emission wavelengths from 300 to 650 nm. Two photomultiplier tubes are used to detect fluorescence from each well in a column of 8 wells allowing for continuous emission ration detection. The blue-sensitive bi-alkali photomultiplier tube is typically used to detect the shorter wavelength emission while the multi-alkali photomultiplier tube is used to detect longer wavelength emission.

The vertical position of the fibers is adjusted by a stepper motor driven cam system. The fibers are lowered when the plate is moved in or out of the system to allow the skirt of the microplate to pass over the fibers. The fibers are raised once the plate is in the system to maximize fluorescence detection efficiency.

The microplate carrier is extended through a trap door 112 by a stepper motor driven translation stage to receive microplates from either the robotic system or a manual operator.

The liquid handler is then triggered via the multifunction board I/O feature to add reagent to the wells while fluorescence is continually read. The plate is then moved to the next column where this process is repeated. Each column is read in this manner until the whole plate has been read. The plate is then extended out of the instrument and retrieved by either a robotic system or the manual operator. The system is now ready to receive another plate. The device can be also configured to read in a different manner in which the whole plate is read at once rather than one column at a time. In the "plate assay mode" the whole plate is read a fixed number of times. The plate is then stopped and the Hamilton is triggered to add reagents to the whole plate. The plate is then read for an additional number of times following reagent addition. Upon completion of reading, the plate is once again extended out of the system.

Figure 2:
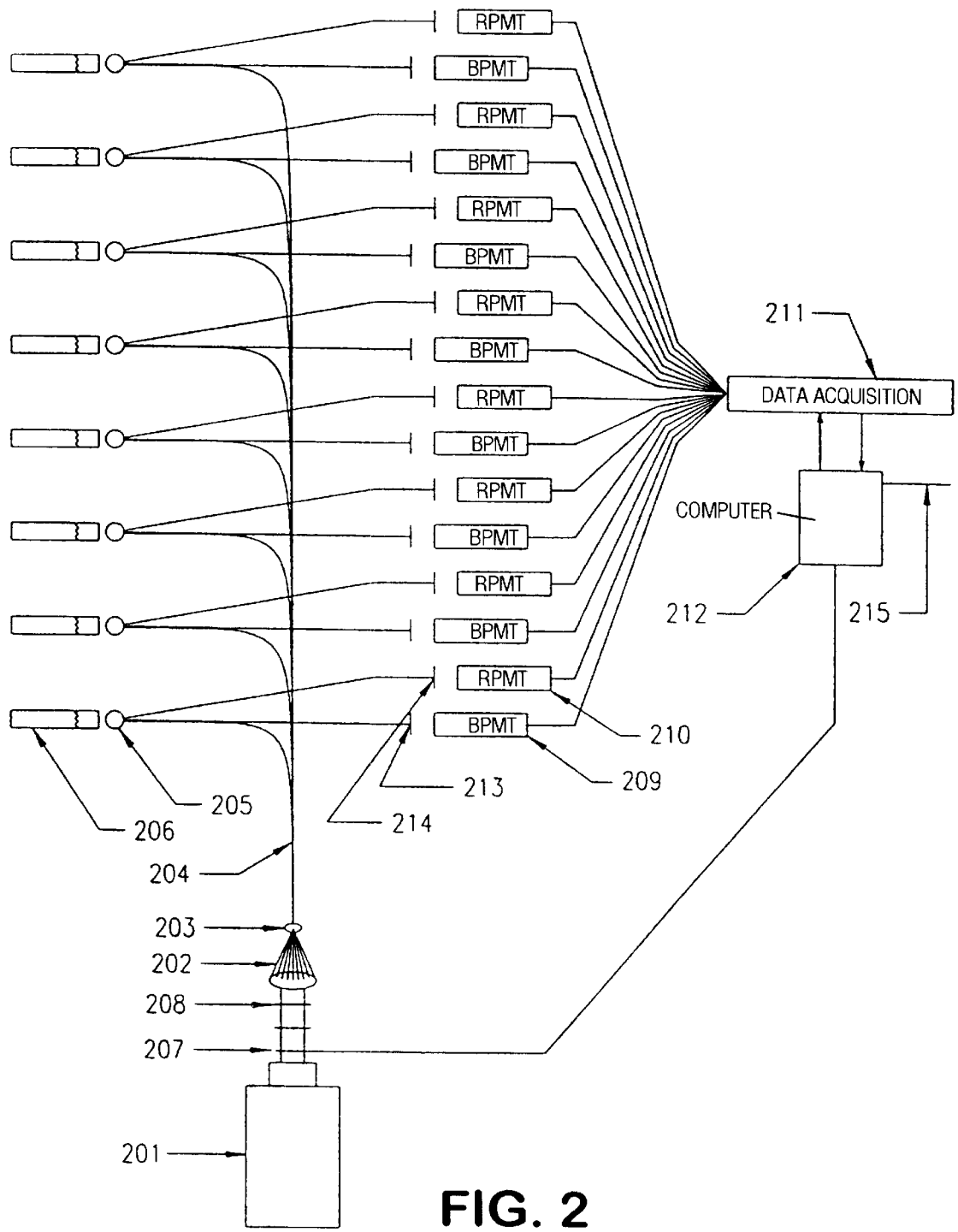
FIG. 2 shows one embodiment of a detection arrangement according to the invention.

Fluorescence can be detected from an interrogation layer if desired using the invention. Referring to FIG. 2, monolayers of cells can be detected on the bottom of microplate wells 206 by the common end of a trifurcated optical fiber bundle 203. One leg of the each trifurcated fiber bundle is used as an excitation source 201; each of the eight excitation legs is fused into a single bundle 204 to provide uniform light intensity to each of the eight trifurcated bundles. The other two legs of the trifurcated fiber are used for to detect fluorescence emission 214 and 213. The common end of the trifurcated bundle is used to both excite and collect fluorescence emission. 8 trifurcated fibers are used to detect two emission channels from each well in a column of 8 wells. A ball lens 205, (RB-707004, Bird Precision, Waltham, Mass.) is at the top of the common end of the trifurcated fiber bundle to increase the efficiency of fluorescence detection.

A 300 watt xenon arc lamp 201, CXP300, ILC Technology, Sunnyvale, Calif.) with a parabolic reflector can be used as the fluorescence excitation source. The excitation light is filtered by two 2" diameter interference filters (400RDF15 or 480RDF20, Omega Optical, Brattleboro, Vt.) and then focused by a lens 202 on to the excitation leg of the trifurcated bundle. Both a IR heat absorbing water filter 207 and shutter system 208 are also included in the optical path to protect the interference filters from heat damage. A 1" diameter "head-on" photomultiplier (HC124 series, Hamamatsu Corp, Bridgewater, N.J.) tubes are used to detect the fluorescence emission. Fluorescence emission from one leg of the fiber bundle is detected by a blue-sensitive bi-alkalai photomultiplier tube 209; emission from the other leg of the fiber bundle is detected by a red-sensitive multi-alkalai photomultiplier tube 210. Data is collected by the A/D portion of a multifunction board (PCI-MIO-E-1, National Instruments, Dallas, Tex.) in a pentium based personal computer 212. The computer controls data acquisition, plate and fiber movement, and shutter opening and closing 215.

The device can utilize a Hamilton Mircolab 2000 8-channel automated liquid handler to add reagents to the top of a 96 well plate. The Hamilton Eclipse software allows the user to change parameters such as reagent volume, speed of reagent addition, height at which reagents are added, and wash cycle length. Example programs are provided for the user to customize for their assay. Separate positions are provided for the 96 well assay plate and a 96 well plate containing compounds. A typical assay where each column is read for 35 seconds takes about 7.3 minutes per plate allowing for 30 plates to be read in less than 4 hours. The fastest the system can be run using current liquid addition and washing protocols is 20 seconds per column or 4.3 minutes per plate allowing for 30 plates to be read in about 2.5 hours.

Components of the Detection System

Typically, the greatest issue in fluorescent detection is the reduction of background signal in the detection system. In this case the detection system might comprise the excitation source and associated optics (dichroic filters, interference filters, focussing lenses, collimators etc), the fiber optic assembly (exicitation and emission pathways and patterns), the substrate containing sample to be analyzed, and the emission filters and associated optics that direct the emission radiation to the detection element. A key challenge in epifluorescent detection (where the excitation light and emission light are directed and collected from the same plane) is to maximize the excitation light energy and the area (the field of view created by the excitation light) this energy is delivered to the sample without comprising the efficient collection of the fluorescent emission or generating a high background from the reflection of excitation radiation. Typically, a tradeoff exists between optimal radiant energy, the field of view illuminated by the excitation energy and the fluorescent emission collection efficiency. For example, the wavelength to be utilized for excitation may preclude the use of certain materials (which might have other desirable features like high NA) due to the incompatibility of the material (high autofluorescence) with the excitation wavelength that is required.

Fiber optic bundles are created with varying packing patterns of excitation and emission bundle arrangements, and with different numbers of fibers in the excitation leg and dual emission legs. In one embodiment, the packing of the fibers of both the excitation and emission legs in the bundle is randomly packed. In another embodiment the fibers are arranged in specific and defined patterns, that confers a preferred optical characteristic to the system. For example, the excitation fibers could be bundled to together centrally in the fiber optic bundle and the emission filters arranged around the outside to create a coaxial fiber optic bundle. Alternatively, the emission bundles could be arranged in small groups to create an array, or radially around the axis of the bundle, or any other symmetrical or non-symmetrical pattern.

Fiber optic assembles may also vary in total number of fibers of both the excitation and emission legs and overall size. The number of excitation fibers and the number of emission fibers and the relative ratios of excitation fibers to emission fibers may be widely varied depending upon the other components in the system, as well as the type of light source, sensitivity of the detector and size of the addressable well in which the sample is located. The optimization of these factors is discussed herein. In one embodiment a fiber optic bundle may contain a total of 341 fibers of which 55 will be excitation fibers arranged randomly within the fiber. In another embodiment the fiber may have 341 fibers of which 85 fibers are excitation fibers arranged in preferentially within the center of the bundle, but also distributed randomly through the remainder of the emission bundles. In another embodiment the fiber may contain 112 fibers of which 7 fibers are excitation fibers arranged in the center of the bundle, and the remaining emission fibers are located around the excitation fibers. In another embodiment the fiber may contain 1417 fibers of which 163 fibers are excitation fibers arranged in the center of the bundle, and the remaining emission fibers are located around the excitation fibers. In another embodiment of the fiber optic bundle, the excitation fibers are centrally located within the bundle and extend beyond the point where the emission fibers terminate. In a preferred version of this embodiment the emission filters terminate into a liquid light guide that is in contact with the ball lens.

Ball lens compositions of materials of different refractive index and of different sizes can be easily evaluated with each fiber optic arrangement to establish a preferred optical arrangement. Ball lens of about 1 mm, 2 mm, 3 mm, 4 mm, 5 mm, 6 mm, 8 mm, 10 mm and 20 mm diameter may be evaluated depending on the size of the instrument and spatial requirements of the imaging system desired. Suitable compositions of the ball lens include fused silica, sapphire, optical glass (such as BK7, SF11 or LaSF9), borosilicate glass or zinc selenide (for infrared applications). Preferred compositions of the ball lens for use within the wavelength range 300–750 nm include fused silica and sapphire. For low light applications it is often necessary to include a suitable anti-reflective coating such as single or multi-layer $MgF_2$, V-coatings, HEBBARTM™ (High Efficiency BroadBand AntiReflection) and Extended range AntiReflective coatings for a ball lens. To determine the optimum composition, size and AntiReflective coating (AR) coating of the lens different coatings, each size of ball lens above made of each of the materials above would be prepared with each of the AR coatings above, and in the absence of an AR coating.

To select the preferred optical components for a specific application it is often preferred to determine the signal to noise (S/N) level for particular combinations of ball lens and fiber optic assemblies. Signal to noise ratios can be determined by comparing the magnitude of a defined amount of fluorescent material measured in the optical system, compared to the noise obtained by measuring an empty well under exactly the same conditions. S/N ratios can be calculated at a range of concentrations of the calibration material (for example, fluorescein) to determine overall detector sensitivity and linearity. Additionally, variability of measurements can be expressed in terms of standard deviation (S.D.) and Coefficient of Variance (C.V.) to establish reproducibility and alignment sensitivity of each of the systems.

Additionally, it is preferred to select the spacing of the fiber optic bundle to the ball lens and the ball lens to the surface of the object to be interrogated. This can be quickly accomplished by generating a graph of S/N ratio versus distance for each of the optical arrangements desired. In the same way, similar S/N ratio graphs can be created for each of the combinations in response to different illumination intensities and wavelengths of excitation light (in conjunction with appropriate fluorescent samples). This analysis would create a matrix of performance characteristics as represented by S/N ratios that are used to select the optimal fiber optic assemblies, ball lens size, composition, antireflective coating, and spatial alignments of the components for specific applications.

Detectors

The detector can include a photon sensitive surface or material for measuring photon emission, such as a CCD, photodiode, or a PMT. The detector can intensify the signal, and gate if desired, using a photon intensifier. Preferably, the detector can utilize a high quantum efficiency CCD without an intensifier for long detection integration. Alternatively, the detector can utilize PMT's or multi-site PMT's for photon detection and quantitation.

The detector preferably functions in the epi-fluorescence mode where the preferred illumination is from the bottom of the multiwell plate and the preferred collection is also from the bottom of the multiwell plate. The detector usually is capable of three to four orders of magnitude of dynamic range in signal response from a single reading. The detector, in a preferred embodiment, utilizes a CCD chip for imaging and detecting photons emitted from the assay wells.

Light Source

In the preferred embodiment, the detector comprises a light source assembly (e.g., Xenon) that can be switched between continuous and pulsed (1 kHz) output depending upon power supply. Suitable light sources are described herein and other suitable sources can be developed in the future.

Liquid Handlers

In one embodiment, the liquid handler can comprise a plurality of nanoliter pipetting tips that can individually dispense a predetermined volume. Typically, pipetting tips are arranged in two-dimension array to handle plates of different well densities (e.g., 96, 384, 864 and 3,456).

Usually, the dispensed volume will be less than approximately 2,000 nanoliters of liquid that has been aspirated from a predetermined selection of addressable wells and dispensed into a predetermined selection of addressable wells. Preferably, nanoliter pipetting tips can dispense less than approximately 500 nanoliters, more preferably less than approximately 100 nanoliters, and most preferably less than approximately 25 nanoliters. Dispensing below 25 nanoliters can be accomplished by pipetting tips described herein. Preferred, minimal volumes dispensed are 5 nanoliters, 500 picoliters, 100 picoliters, 10 picoliters. It is understood that pipetting tips capable of dispensing such minimal volumes are also capable of dispensing greater volumes. The maximal volume dispensed will be largely dependent on the dispense time, reservoir size, tip diameter and pipetting tip type. Maximum volumes dispensed are about 10.0 microliters, 1.0 microliters, and 200 nanoliters. Preferably, such liquid handlers will be capable of both dispensing and aspirating. Usually, a nanoliter pipetting tip (or smaller volume dispenser) comprises a fluid channel to aspirate liquid from a predetermined selection of addressable wells (e.g., chemical wells containing drug candidates). Liquid handlers are further described herein, and for some volumes, typically in the microliter range, suitable liquid pipetting tips known in the art or developed in the future can be used. It will be particularly useful to use liquid handlers capable of handling about 1 to 20 microliter volumes when it is desired to make daughter plates from master plates. Preferably, in such instances a liquid handler has a dispensing nozzle that is adapted for dispensing small volumes and can secure a tip having a fluid reservoir.

In one embodiment nanoliter pipetting tips comprise solenoid valves fluidly connected to a reservoir for liquid from an addressable chemical well. The fluid reservoir can be a region of a dispenser that can hold fluid aspirated by the nanoliter pipetting tip. Usually, a tip reservoir will hold at least about 100 times the minimal dispensation volume to about 10,000 times the dispensation volume and more preferably about 250,000 times the dispensation volume. The solenoid valves control a positive hydraulic pressure in the reservoir and allow the release of liquid when actuated. A positive pressure for dispensation can be generated by a hydraulic or pneumatic means, e.g., a piston driven by a motor or gas bottle. A negative pressure for aspiration can be created by a vacuum means (e.g., withdrawal of a piston by a motor). For greater dispensing control, two solenoid valves or more can be used where the valves are in series and fluid communication.

In another embodiment, nanoliter pipetting tips comprise an electrically sensitive volume displacement unit in fluid communication to a fluid reservoir. Typically, the fluid reservoir holds liquid aspirated from an addressable chemical well. Electrically sensitive volume displacement units are comprised of materials that respond to an electrical current by changing volume. Typically, such materials can be piezo materials suitably configured to respond to an electric current. The electrically sensitive volume displacement unit is in vibrational communication with a dispensing nozzle so that vibration ejects a predetermined volume from the nozzle. Preferably, piezo materials are used in dispensers for volumes less than about 10 to 1 nanoliter, and are capable of dispensing minimal volumes of 500 to 1 picoliter. Piezo pipetting tips can be obtained from Packard Instrument Company, Connecticut, USA (e.g., an accessory for the MultiProbe 104). Such devices can also be used in other liquid handling components described herein depending on the application. Such small dispensation volumes permit greater dilution, conserve and reduce liquid handling times.

In some embodiments, the liquid handler can accommodate bulk dispensation (e.g., for washing). By connecting a bulk dispensation means to the liquid handler, a large volume of a particular solution to be dispensed many times. Such bulk dispensation means are known in the art and can be developed in the future.

Positioners, Transitional Stages

Interrogation, aspiration or dispensation into multiwell plates of different densities can be accomplished by automated positioning (e.g. orthogonal) of a multiwell plate. Typically, the multiwell plates are securely disposed on an orthogonal positioner that moves the wells of a multiwell plate with a first density in an X,Y position with respect to the X,Y position of the liquid handler. Usually, the liquid handler will have an array of aspiration and/or dispensation heads, or both. Many aspiration/dispensation heads can operate simultaneously. The orthogonal positioner will align each addressable well with the appropriate dispensing head. Preferably, a predetermined location (e.g., center) of a pre-selected addressable well will be aligned with the center of a dispensing head's fluid trajectory. Other alignments can be used, such as those described in the examples. With a head substantially smaller than a well diameter, orthogonal positioning permits aspiration or dispensation into plates of different densities and well diameters.

An orthogonal positioner can typically match an array of dispensing heads with an array of addressable wells in X,Y using a mechanical means to move the addressable wells into position or the liquid handler (e.g., dispensing heads) into position. Preferably, arrays of addressable wells on a plate are moved rather than the liquid handler. This design often improves reliability, since multiwell plates are usually not as heavy or cumbersome as liquid handlers, which results in less mechanical stress on the orthogonal positioner and greater movement precision. It also promotes faster liquid processing times because the relatively lighter and smaller multiwell plates can be moved more quickly and precisely than a large component. The mechanical means can be a first computer-controlled servo motor that drives a base disposed on a X track and a second computer-controlled servo motor that drives a Y track disposed on the X track. The base can securely dispose a multiwell plate and either a feedback mechanism or an accurate Cartesian mapping system, or both that can be used to properly align addressable wells with heads. Other such devices, as described herein, known in the art or developed in the future to accomplish such tasks can be used. Usually, such devices will have an X,Y location accuracy and precision of at least ±0.3 mm in X and ±0.3 mm in Y, preferably of at least ±0.09 mm in X and ±0.09 mm in Y, and more preferably of at least ±0.01 mm in X and ±0.01 mm in Y. It is desirable that such devices comprise detectors to identify the addressable wells or multiwell plates being orthogonally positioned. Such positioners for predetermined X, Y coordinates can be made using lead screws having an accurate and fine pitch with stepper motors (e.g., Compumotor Stages from Parker, Rohnert Park, Calif., USA). Positioners (eg. X, Y or Z) can be used to move the detector assembly, the sample, liquid handler or a combination there of.

Alternatively, the liquid handler can be disposed on a Z-positioner, having an X,Y positioner for the liquid handler in order to enable precise X,Y and Z positioning of the liquid handler (e.g., Linear Drives of United Kingdom).

A reference point or points (e.g., fiducials) can be included in the set up to ensure that a desired addressable well is properly matched with a desired addressable head. For instance, the multiwell plate, the orthogonal positioner or the liquid handler can include a reference point(s) to guide the X,Y alignment of a plate, and its addressable wells, with respect to the liquid handler. For example, the liquid handler has a detector that corresponds in X,Y to each corner of a plate. The plate has orifices (or marks) that correspond in X,Y to the liquid handler's position detectors. The plate's orifices allow light to pass or reflect from a computer-controlled identification light source located on the orthogonal positioner in the corresponding X,Y position. Optical locators known in the art can also be used in some embodiments (PCT patent application WO91/17445 (Kureshy)). Detection of light by the liquid handler emitted by the orthogonal positioner verifies the alignment of the plates. Once plate alignment is verified, aspiration or dispensation can be triggered to begin. Stepper motors can be controlled for some applications as described in U.S. Pat. No. 5,206,568 (Bjornson).

The liquid handler will also typically be disposed on a Z-dimensional positioner to permit adjustments in liquid transfer height. This feature allows for a large range of plate heights and aspirate and dispense tips, if desired, to be used in the sample distribution module. It also permits the dispense distance between a addressable well surface, or liquid surface in an addressable well, and a liquid handler to be adjusted to minimize the affects of static electricity, gravity, air currents and to improve the X,Y precision of dispensation in applications where dispensation of a liquid to a particular location in a addressable well is desired. Alternatively, multiwell plates can be positioned on a Z-dimensional positioner to permit adjustments in liquid transfer height. Static neutralizing devices can also be used to minimize static electricity. Generally, the liquid transfer height will be less than about 2 cm. Preferably, small volumes will be dispensed at a liquid transfer height of less than about 10 mm, and more preferably less than about 2 mm. Occasionally, it may be desirable to contact the tips with a solution in a controllable fashion, as described herein or known in the art Control, Data Processing and/or Integration Modules In one embodiment, a data processing and integration module can integrate and programmably control a liquid handler module, a moving conveying surface, and a detector module to facilitate rapid processing of the multiwell wells. To manage information in the system, the data processing and integration module comprises elements to store, manage and retrieve data, including a data storage device and a processor. The data storage device can hold a relational database, an array of physical disk drives (e.g., random access disk drives), and a connection to other system components via a network. A data storage device can, for instance, store a relational database for environmental, diagnostic, and drug discovery applications. For instance, one particularly useful relational database can be provided by Oracle, and the network can be a TCP/IP (transfer communication protocol) ethernet LAN (local area network).

Software Controls

The system can be controlled using supervisory control programs, which are not necessarily located on the same computer as the data storage device. For example, in one embodiment of a system, a separate supervisory control computer is provided for each of the Storage and Retrieval, Reagent Transport, and Reagent Distribution functions. A supervisory control computer is a computer programmed to control a particular subsystem using data from the data storage device and operating on a workstation or component, such as a storage and retrieval, reaction module or sample transporter. Within the data storage device, exists a structure for information in the form of tables and relations. This structure is designed to meet the specific needs of the system, wherein it must accommodate the throughput demands of an automated system and facilitate the presentation of information for analysis and visualization of results. The data storage device can typically process in excess of 100,000 transactions (read or write particular data) per day, while accurately keeping track of every chemical, biological reagent, operation, unit of work and workstation and other related activities. Integrity of the data storage device is typically maintained for simultaneous multiple users and processes. Information in the relational database of the data storage device is used to define operations to be performed, and a complete audit trail can be maintained of every operation on every unit of work throughout the system.

Storage devices suitable for use with the present invention are well known and are commercially available from a number of manufacturers, such as the 2 gigabyte Differential System Disk, part number FTO-SD8-2NC, and the 10 gigabyte DLT tape drive, part number P-W-DLT, both made by Silicon Graphics, Inc., of Mountain View, Calif., or equivalents (e.g., optical discs). A preferred embodiment uses Hewlett Packard 4 GB Hot Swap Drives in a Netserver LX Pro configured as RAID-5

Interface Designs

In most embodiments, it will be advantageous to integrate and operably link device of the invention with at least one other workstation, usually a sample transporter. The integration can be accomplished with a computer and associated control programs to instruct the translational stage and sample processor to operate coordinately. Alternatively, the device may be used without directly integrating to another workstation by tracking addressable wells in groups and either mechanically or manually transporting multiwell plates to another work station where the multiwell plates are identified. For instance, the device of the invention may be directly integrated and operably linked to a storage and retrieval module and sample transporter, and indirectly linked to a integration and control module. While this approach is feasible, especially for lower throughputs, it is not desirable for higher throughputs as it lacks direct integration that can lead to faster throughput times. Manual operations also are more frequently subject to error especially when processing large numbers of samples. Preferably, the device of the invention can be integrated with other workstations and operate in a mode with minimal or substantially no manual intervention related to transferring multiwell plates to other work stations.

Usage Modes

The detector is often capable of many different operating modes that facilitate drug discovery assay requirements. These operating modes can include: single excitation wavelength with single emission wavelength detection, single excitation wavelength, dual emission wavelength detection, sequential dual excitation wavelength with dual emission wavelength detection and ratio measurement determination, sequential dual excitation wavelength with four emission wavelength detection and ratio measurement determination, homogeneous time resolved fluorescence with single excitation wavelength and single emission wavelength detection, homogeneous time resolved fluorescence with single excitation wavelength and dual emission wavelength detection and ratio determination measurement, homogeneous time resolved fluorescence with sequential dual excitation wavelength and dual emission wavelength detection and ratio determination measurement, absorbance (e.g. dual), transmittance (e.g. dual), reflectance, dual sequential excitation wavelengths and single emission wavelength detection with ratio determination measurement, luminescence measurement at a single wavelength with luminescence measurement at dual wavelengths, luminescence measurement at dual wavelengths with a ratio determination, and time resolved fluorescence emission (intrinsic dye properties with or without a binding event).

Software and Data Collection

A windows based graphical user interface can be used with the invention. The software calls routines, which will either setup the instrument, test the instrument, run manual assays, run automated assays, or analyze data. Users can change such parameters as how long data is acquired, how compound additions are performed, and when in the time trace the compound is added. A safety feature to check whether a plate has been loaded can also be set in the control screen. Manual test functions include moving the 96 well plate in and out, raising and lowering the optical fibers, and reading fluorescence values. Assays can be run in two different formats as discussed in the hardware section. The experiments can be controlled by a Sagian robotic system or by a manual user. The user can also change liquid addition parameters such as volume of reagent added or speed of liquid addition in the Hamilton Microlab 2200 software.

Raw intensity values for both emission wavelengths can be plotted in real-time. Data can be analyzed and the result displayed immediately following the completion of an experiment. Both raw and processed data files are saved as ASCII text. The data files can be imported by spreadsheet programs (e.g. Excel) for further analysis. Software and hardware have been provided to allow a robotic system to load and remove both compounds and assays plates. Software to allow the user to optionally introduce a manual bar code reader has also been included.

Fluorescence Measurements

It is recognized that different types of fluorescent monitoring systems can be used to practice the invention with fluorescent probes, such as fluorescent dyes or substrates. Preferably, systems dedicated to high throughput screening, e.g., 96-well or greater microtiter plates, are used. Methods of performing assays on fluorescent materials are well known in the art and are described in, e.g., Lakowicz, J. R., *Principles of Fluorescence Spectroscopy*, New York: Plenum Press (1983); Herman, B., Resonance Energy Transfer Microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219–243; Turro, N. J., *Modern Molecular Photochemistry*, Menlo Park: Benjamin/Cummings Publishing Col, Inc. (1978), pp. 296–361 and the Molecular Probes Catalog (1997), OR, USA.

Preferably, FRET (fluorescence resonance energy transfer) is used as a way of monitoring probes in a sample (cellular or biochemical). The degree of FRET can be determined by any spectral or fluorescence lifetime characteristic of the excited construct, for example, by determining the intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor. For example, cleavage of the linker increases the intensity of fluorescence from the donor, decreases the intensity of fluorescence from the acceptor, decreases the ratio of fluorescence amplitudes from the acceptor to that from the donor, and increases the excited state lifetime of the donor. Preferably, changes in signal are determined as the ratio of fluorescence at two different emission wavelengths, a process referred to as "ratioing." Differences in the absolute amount of probe (or substrate), cells, excitation intensity, and turbidity or other background absorbances between addressable wells can affect the fluorescence signal. Therefore, the ratio of the two emission intensities is a more robust and preferred measure of activity than emission intensity alone.

EXAMPLES

Example 1

Construction and Testing of a Ball Lens Trifurcated Fiber Optic Assembly

Arrangements of ball lenses and trifurcated fibers can be tailored to their intended application. To determine the appropriate arrangement of fiber optic bundles and ball lens a series of experiments can be conducted to determine the highest signal to noise ratio, preferred sensitivity, lowest background, preferred field of optical interrogation or excitation or a combination thereof.

For example, one embodiment of a trifurcated fiber optic assembly adapted for miniaturized sample analysis of a 1 mm well diameter with a variable interrogation layer of approximately 0.1 mm to 2.0 mm could comprise the following arrangement. A ball lens made of fused silica material coated with an antireflective coating such as HEBBAR, with a diameter of about 3 mm. A trifuricated fiber optic assembly, optically coupled to the ball lens comprising 91 fibers of which 7 fibers in the center are for excitation and the remaining fibers are for emission collection. The fiber assembly being about 3 mm in diameter and packed into a hexagonal ferrule to maximize packing efficiency and ease of assembly. The emission fibers (41 for each optical property to be measured) are selected so as to maximize collection efficiency, signal intensities and signal to noise or signal to background) properties of the assembly. The following table illustrates the effect that the spatial position of the ball lens to the fiber assembly has on Signal-to-background. In this example, the distance of the ball lens to the test fluorescent sample was kept constant as the distance of the ball lens to the fiber optic assembly was varied. Different signal to background ratio's were obtained from which an optimal distance could be selected.

TABLE 1

Emission filter: 535RDF30 (no long pass)
Sample volume: 2 microliters, hand loaded.
Ball lenses: Fused silica.

| Distance from lens to plate = 0. | | | | (Signal − background)/ |
|---|---|---|---|---|
| Fiber-to-lens (mm) | Empty (mV) | Buffer (BB) Background | 10 nM F Signal | background (10 nM F − BB)/BB |
| 0 | 10.8 | 12.4 | 119 | 9 |
| 0.384 | 9 | 7.95 | 117.67 | 14 |
| 0.482 | 7.8 | 6.95 | 130.33 | 18 |
| 0.533 | 8 | 7.25 | 126 | 16 |
| 0.584 | 7.9 | 7.15 | 122 | 16 |
| 0.71 | 4.9 | 5.8 | 34 | 5 |

Subsequent further analysis of this particular system demonstrates an optimal distance for the test sample relative to the ball lens fiber optic assembly between about 0 and 0.152 mm.

TABLE 2

Distance from fiber to lens = 0.584 mm

| lens-to-plate (mm) | Empty (mV) | Buffer (BB) (mV) | 10 nM F (mV) | (10 nM F − BB)/BB |
|---|---|---|---|---|
| 0 | 7.9 | 7.15 | 122 | 16 |
| 0.152 | 7.8 | 7.2 | 126 | 17 |
| 0.203 | 8.4 | 8.15 | 119.5 | 14 |
| 0.305 | 10 | 8.9 | 118 | 12 |

Figure 3:
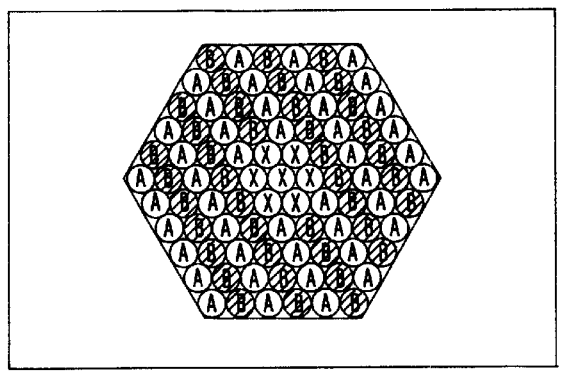
FIG. 3 shows a cross sectional view of the fiber optic bundle showing potential arrangements of the individual fiber optic fibers. Excitation fibers being represented by X or cross hatching, and emission fibers being represented by the letters A for the first emission leg of the fiber optic bundle, and B, for the second emission leg fiber optic bundle.
Figure 3:
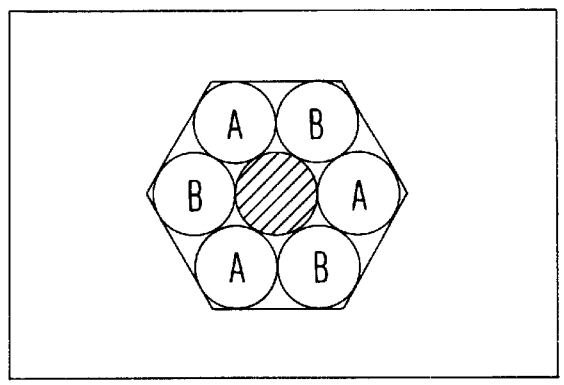
Figure 3:
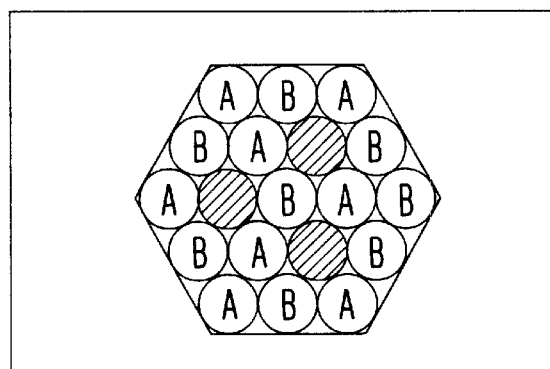
Figure 3:
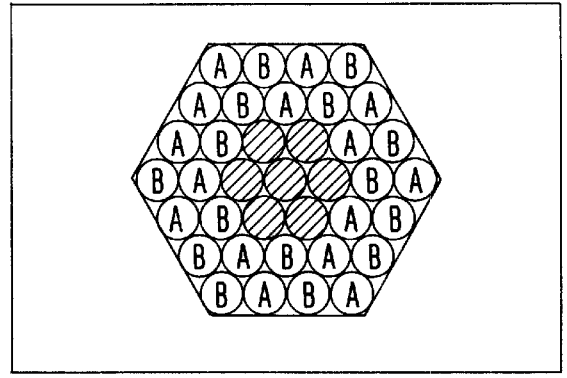
Figure 4:
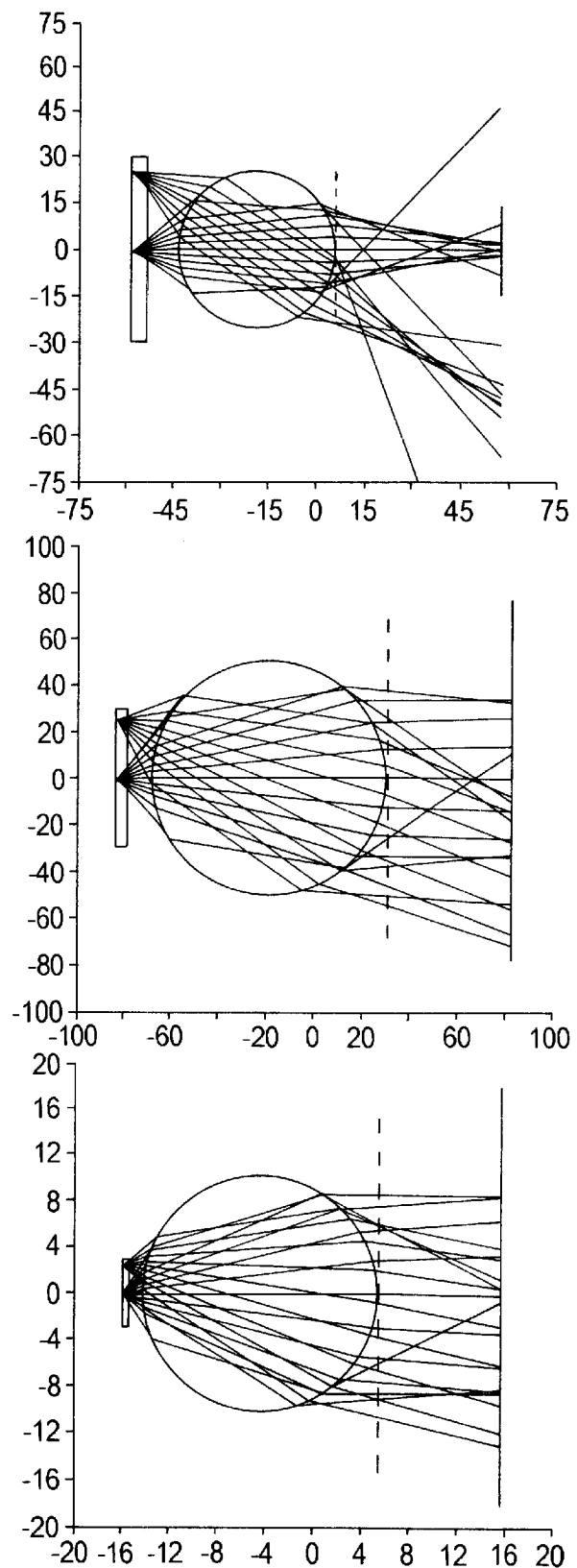
FIG. 4 shows several embodiments of the ball lens of the invention in a cross sectional view depicting the light directing ability of the lens.
Figure 5:
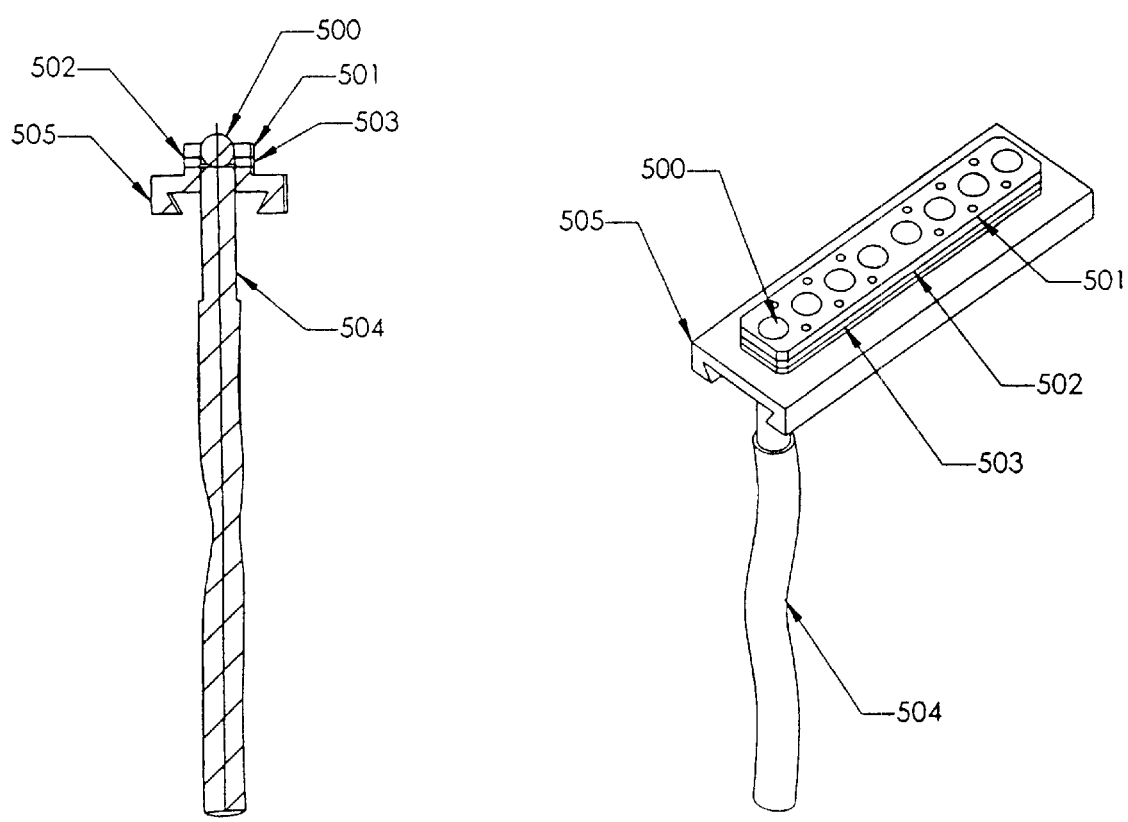
FIG. 5 shows a perspective view of one embodiment of the ball lens assemblies of the present invention. The ball lens 500, ball lens holding assembly, 501 & 502 spring 503, fiber optic bundle 504, and mounting assembly for the assembly 505.
Figure 6:
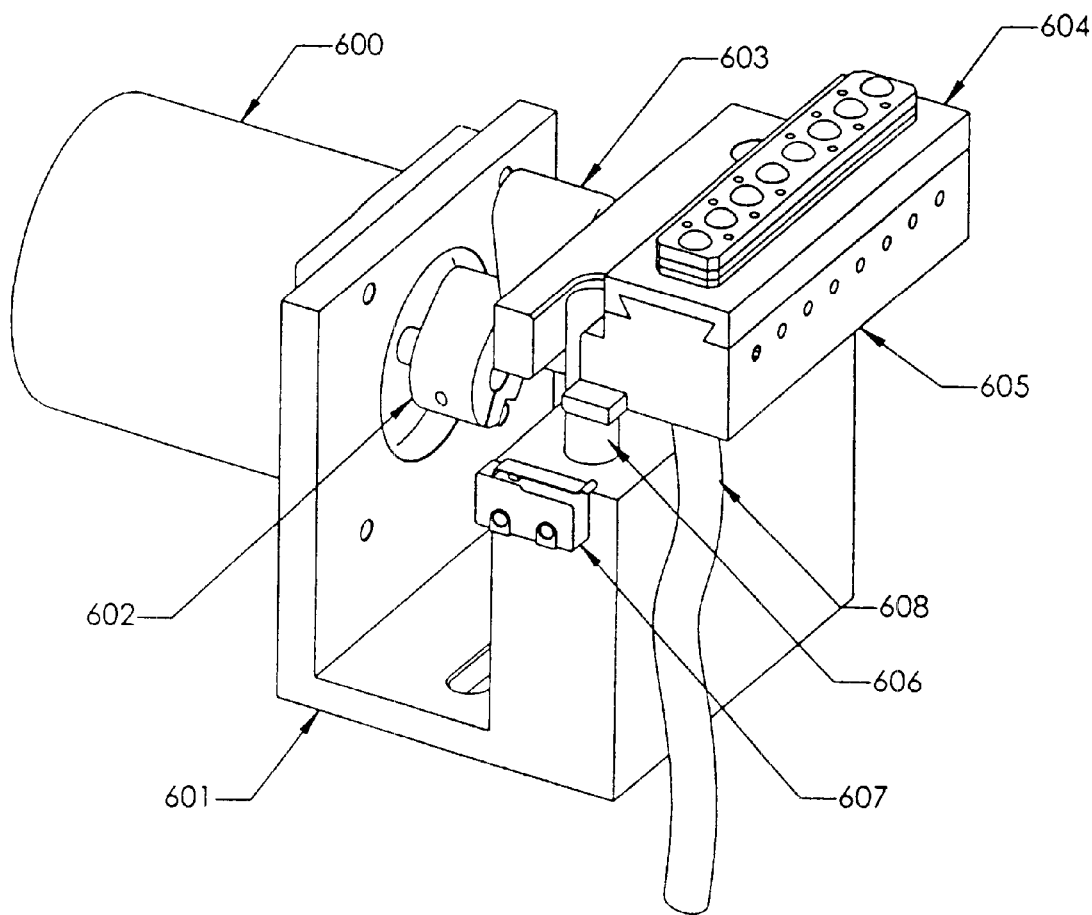
FIG. 6 shows a perspective view of one embodiment of the ball lens assembly Z-axis mover according to the invention. The stepper motor 600, z-axis mounting assembly 601, cam 602 & 603, ball lens assemblies 604, platform for ball lens assemblies 605, guiding pillar 606, switch 607, and trifurcated fiber optic bundle 608.

In one example a 3 mm Hebbar coated sapphire ball lens was utilized with four different 665 fiber optic assemblies (as shown in FIG. 3) to assess performance as measured by minimum detectable level of signal for the particular dye being tested as described herein.

TABLE 3

| Description of Assembly | Detectable signal in nM of Fluorescein | Number of Ex Fibers | Number of Em Fibers | Fiber Assembly Diameter |
|---|---|---|---|---|
| Assembly #1 | 0.50 | 7.00 | 84.00 | 2.6 mm |
| Assembly #2 | 0.86 | 1.00 | 6.00 | 1.2 mm |
| Assembly #3 | 0.50 | 3.00 | 16.00 | 1.5 mm |
| Assembly #4 | 0.50 | 7.00 | 30.00 | 1.6 mm |

Surprisingly, assemblies #3 and #4 perform as well as assembly #1. This indicates that the optimal ball lens size can be typically about equal or 1 to 3 times greater in diameter than the fiber optic assembly. The ball lens can thus aid in reducing the complexity or quantity of fibers required in a fiber optic assembly for optimal detection sensitivity particularly when the need to reduce the size of the fiber optic assembly is important in a miniaturized system.

In a similar example to above, the fiber assembly is kept constant but the size of the ball lens is varied. In this example a 3 mm diameter coaxial fiber optic assembly containing 112 fibers arranged with 7 XXF200/210/235T Fused Silica excitation fibers in the center of the assembly surrounded by 105 XXF200/210/235T Fused Silica emission fibers. 3 different size sapphire ball lenses are compared, a 3 mm lens, a 5 mm lens and a 10 mm lens. As the table illustrates, sensitivity as measured by detectable levels of a fluorescent dye improves as ball lens size increases by a factor of 15 in moving from a 3 mm ball lens to a 10 mm ball lens.

TABLE 4

Different Size Ball Lens

Experiment Description
Glass Bottom Plate with Solution Standards
Cermax 300 w Xenon Lamp,

| dual excitation and emission filtering Sapphire Ball Lens with HEBBAR coating | Relative Sensitivity Molar equivalents of dye |
|---|---|
| PMT - 3 mmCoAX - 10 mmHB-DF | 1.125E-12 |
| PMT - 3 mmCoAX - 5 mmHB-DF | 1.108E-11 |
| PMT - 3 mmCoAX - 3 mmHB-DF | 1.727E-11 |

Protocols, Materials and Methods for the Experiments Herein

MDL1, minimum detectable level (MDL), is determined from the variance of readings from many buffer blanks and would be affected by well to well variability, positioning artifacts and other errors.

MDL2 is determined from the variance of repeated measurements of the same buffer blank and presumably would be affected only by the noise of the detector.

The fiber optic assemblies were composed of fused silica coated with a black polyimide coating obtained from Fiberguide. The individual fibers are 200/220/240 in microns in diameter for the core/cladding/coating respectively unless otherwise specified in particular experiments.

The optical detectors utilized to evaluate fluorescent intensity in the experiments were either a Hamamatsu PMT and associated electronics as described in the Fluorocount instrument or a Hamamatsu HC 135-01/100 Mhz PMT sensor module with embedded micro controller and RS-232-C interface. This sensor operates in the 360–650 nm range. A Labview™ software interface was written to control the PMT and acquire data. When needed, excitation radiant power was measured using a Newport Corporation 1835-C power meter equipped with a 818-UV NIST traceable silicon photodiode detector. The filters used in these experiments were obtained from Chroma Technology Corporation or Omega Optical Inc., with the exception of neutral density filters that were obtained from Oriel Corp. In general and except where noted, all experiments were conducted with the Hamamatsu PMT were double filtered on the excitation and emission ends with a 0.2 neutral density filter sandwiched in between the interference filters. The excitation filters were HQ475/40 +0.2 ND+D480/20x. The emission filters were 535DF35t +0.2ND+535DF.

Three different light supplies were utilized for the experiments and are identified as appropriate in the experimental results section. The first was a Quartz Tungsten Halogen (QTH) light obtained from Cole-Palmer Model #H-41700-00. The second was a Cermax LX-300W xenon Arc with integral parabolic reflector. The third was a 175 watt Xenon Arc lamp with ultra stable power supply from Hamamatsu.

All of the ball lenses were coated with HEBBAR. Experiments with the Hamamatsu PMT were performed on a Newport Corporation optical bench with Vibration dampening. Certain fixtures and mounts were specially made through local machine shops and others were obtained through Newport Corporation.

Three types of plates were utilized. The standard plate is a 96 well black top clear bottom polystyrene plate filled with fluorescent standards. The glass bottom plates were specially modified black polystyrene 96 well plates with 175 micron glass bottoms. 384 well black polystyrene glass bottom plates were utilized for the 384 well readings. These specially modified plates were obtained from polyfiltronics/Whitman.

Example 2

Sensitivity and Background Testing of Optical Assemblies of One Embodiment of the Invention This example demonstrates the ability of the optical assemblies to achieve uniform illumination of the addressable wells while at the same time avoiding illumination of the sides of the well and the illumination of adjacent wells. This leads to reduced background fluorescent signals caused by reflections from the plate and wells and reduces punch through of excitation light through emission filters into detection system, yet enables high sensitivity detection at two wavelengths.

This is exemplified by the determinations of minimum detectability of a number of fluorescent standards. For example, the minimum detectable fluorescein level achieved using a detector incorporating the optical system of the invention was better than 50 pM fluorescein in a standard 96 well plate. Emission was collected at wavelengths centered at both 535 nm and 580 nm. Both a blank solution and a solution containing 2 nM fluorescein were measured. The minimum detectable level (MDL) was calculated by generating a fluorescein calibration curve that enabled the concentration of fluorescein that was equivalent to 4 times the standard deviation of the buffer blank to be calculated. Because the detector typically measures changes of brightness within a single well, the standard deviations for readings within the same well at 1 Hz for eight seconds are given. It was found that the plate material also affected the MDL levels. Both buffer and fluorescein statistics were determined from 100 µL volumes in 40 wells (5 columns of 8 wells) of a 96 well plate.

TABLE 5

Fluorescein MDL levels measured using 480 ± 10 nm excitation 535 ± 17.5 nm and 580 ± 30 nm emission filters.

| Plate bottom material | Glass | Glass | Polystyrene | Polystyrene |
|---|---|---|---|---|
| Emission wavelength | 535 nm | 580 nm | 535 nm | 580 nm |
| MDL (nM fluorescein) | 0.0017 | 0.0085 | 0.034 | 0.072 |

Because the fluorescent dyes typically used with the detector are not excited at wavelengths, more relevant standards are the fluorophores 3-glycine chloro-coumarin (3GCC) and rhodamine 101. MDL measurements were determined for these fluorescent dyes as described above except that a fluorescent dye solution also containing 25 nM fluorophores 3-glycine chloro-coumarin and 4 µM rhodamine 101 was used in place of the fluorescein solution

TABLE 6

Two Dye MDL levels measured both excited using a 400 ± 7.5 nm filter. The 3GCC fluorescence was collected using a 460 ± 22.5 nm filter; the rhodamine 101 fluorescence was collected using a 580 ± 30 nm filter.

| Fluorescent dye | 3GCC | rhodamine 101 |
|---|---|---|
| Plate bottom material | Polystyrene | polystyrene |
| Emission wavelength | 460 nm | 580 nm |
| Excitation Wavelength | 400 nm | 400 nm |
| MDL (nM fluorescent dye) | 0.181 | 20.8 |

Because 400 nm excitation light is not optimal for the efficient excitation of rhodamine 101, the MDL level for this fluorophore is relatively high when compared to those for 3GCC or fluorescein.

A desirable feature of the invention is that the fiber optic bundle and ball lens assemblies enable efficient excitation of the addressable wells, as well as the ability to simultaneously measure at least two optical properties. The average measured excitation intensity at 400 nm emerging through each of the fiber optic bundles and ball lens of the invention is 529±75 µW when using two 400±7.5 nm excitation filters. The light source used was an ILC CXP300 300 watt Xenon arc lamp, with 6.3 mm anti reflection coated fused silica ball lenses at the common ends of each of eight 5.18 mm diameter bundles containing 333 fibers, 111 fibers from each leg of the randomly packed trifurcated bundles. Light power was measured using a measured using a calibrated Newport 1835-C powermeter.

The use of the trifurcated fibers and ball lens system, and the calculation of an emission ratio significantly reduces experimental noise, eliminates relative excitation variability between the 8 fiber optic assemblies in the detector and leads to tighter C.V.s and improves the dynamic range of FRET based assays. A major additional advantage is the removal of addition artifacts to enable continuous measurements during reagent addition. In these phenomena, intensities of cells loaded with fluorescent dye often decline upon reagent addition. This decline in intensity may be due to some cells being washed from the detection area during addition and mixing of reagents. By taking the emission ratio at two separate wavelengths these artifacts are eliminated. In the data set below, a mammalian neuronal cell line was loaded using a FRET based fluorescent dye system. In this example, the majority of the emission change was in the 460 nm channel. For this experiment minelayers of mammalian cells were plated into the first 6 columns of a 96 well plate. The emission intensities measurements were made at two wavelengths and the ratio determined for 35 seconds at 1 Hz for each of the 8 wells in a column. Reagent solutions were added following the $12^{th}$ read of each column. In this example, test cells stimulated by depolarization by addition of 100 µL high potassium solution (90 mM K). Control cells received normal Hank's buffered saline solution (HBS) without high potassium to test for addition artifacts. Both intensity data and emission data were normalized versus basal levels to account for well to well variations in cell number or loading brightness and normalized basal levels prior to reagent addition. This enables direct comparisons between intensity data and ratiometric data.

TABLE 7

Comparison of ratio versus non-ratio measurements Data Normalized to Initial Values

| | Int (460 nm) | Emission Ratio (460/580) |
|---|---|---|
| HBS | | |
| AV | 91.7% | 99.2% |
| SD | 4.0% | 1.4% |
| CV | 4.4% | 1.4% |
| HiK | | |
| AV | 139.3% | 155.6% |
| SD | 6.3% | 4.9% |
| CV | 4.5% | 3.1% |
| Difference | 47.6% | 56.5% |

As can be seen in table x, both the standard deviations and coefficient of variation are about 30% lower for the ratiometric data (1.4% compared to 4.4% for HBS controls). There is also an addition artifact (91.7% of basal) in the intensity data but not in the emission data (99.2% of basal) for the control HBS additions. Because the emission ratio data factors both the increase in intensity at 460 nm and the slight decrease in intensity at 580 nm upon depolarization with HiK solution, the dynamic range of the emission ratio data is larger than that of the single intensity data. Statistics were determined from 24 wells (3 rows of 8 wells).

Example 3

Determination of Na+ Dependent Depolarization in Mammalian Cells

An advantage of the use of the optical assemblies of the invention is the ability to rapidly measure two wavelengths simultaneously thereby enabling the rapid analysis of cellular responses. In the field of voltage sensing, the use of rapid depolarization measurements has several significant advantages over earlier relatively slow depolarization approaches that are subject to artifacts and reduce throughput of the assay. The use of the device thus allows the development of sensitive and rapid assay systems for membrane voltage measurements in whole cells. These assays are highly sensitive, reliable and able to discriminate relatively small changes in membrane potential with high precision.

Mammalian neuronal cells were grown in F12 complete medium supplemented with 20% fetal bovine serum. Prior to experiments cells were washed twice with sodium free buffer (140 mM N-methyl-D-glucamine, 10 mM HEPES, pH 7.2, 0.34 mM $Na_2HPO_4$, 0.4 mM $MgCl_2$, 0.5 mM $KH_2PO_4$, 5.37 mM KCl, 1.26 mM $CaCl_2$, 2 g/L D-glucose). The cells were then harvested using calcium and magnesium free buffer and washed once. The cells were then loaded with the fluorescent dye CC1-DMPE (4 $\mu$M for 30 minutes at room temperature) and washed in sodium free buffer. The fluorescent dye $DiSBAC_2$ was then added to the cells, after 30 minutes the plates were loaded onto the device of the invention. All wells treated with a channel opener to open $Na^+$ channels and maintained in low $Na^+$ solution. Each well contained approximately $10^5$ cells. The average, standard deviation, and standard error of the mean are given in the Table 8.

TABLE 8

|  | 0 Na | HBS | HBS-TTX |
|---|---|---|---|
| AV | 99.5% | 130.2% | 98.9% |
| SD | 0.9% | 4.3% | 0.9% |
| C.V. | 0.9% | 3.3% | 0.9% |
| Difference | N/A | 30.7% | −0.6% |

Example 4

Determination of Dose Response Relationships

Figure 8A:
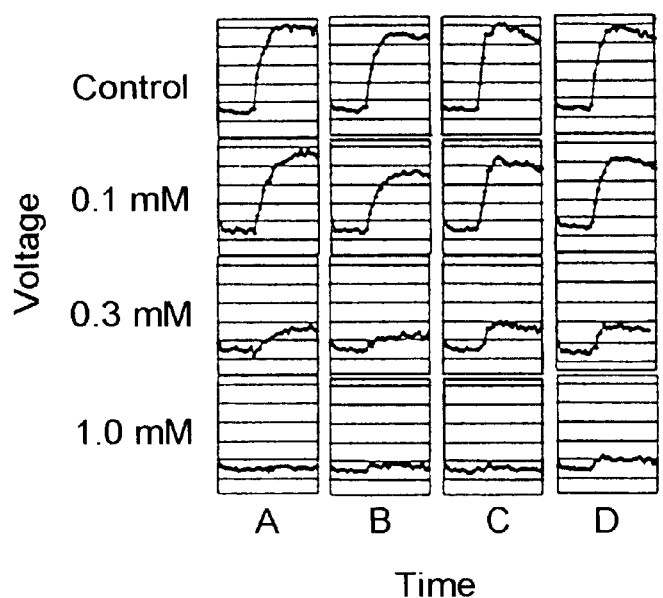
FIG. 8A shows the rapid detection and continuous analysis of voltage changes induced within a cell measured using one preferred embodiment of the invention.

The large ratio changes observed with this method enable the creation of highly reproducible assays and provide signals large enough for dose response curves to be generated. Furthermore because the device can acquire data continuously, the responses from the individual wells can be viewed as a function of time. FIG. 8A shows the real time changes in voltage for individual wells.

Figure 8B:
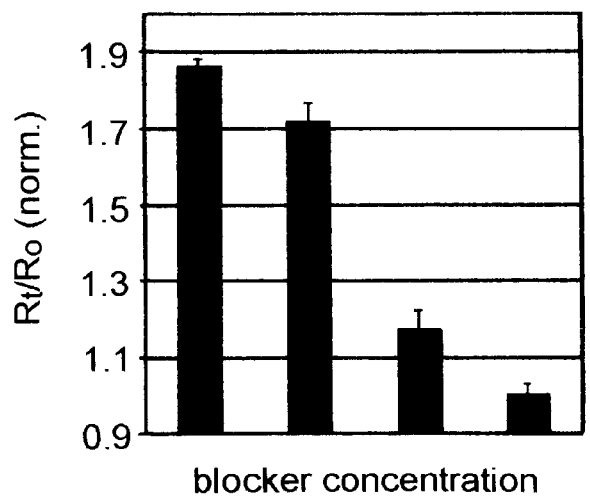
FIG. 8B shows a dose response curve of voltage changes induced within a cell measured in response to the addition of an ion channel blocker, using one preferred embodiment of the invention.

The cells were stained and handled as described in Table 8. All wells contained a sodium channel agonist. Traces show the effect of different doses of an anesthetic RS-105914-197 on blocking $Na^+$ channel activity in the neuronal cells. FIG. 8B shows the dose response of the anesthetic RS-105914-197 for blocking sodium channel activity using the device of the invention. The data represents the average of 4 wells and the error bars represent the CV value. 1 mM of the drug completely blocks the $Na^+$ induced depolarization. These results with error analysis are summarized in Table 2.

TABLE 2

|  | Mean | S.D. | C.V. |
|---|---|---|---|
| 0 mM RS-105914-197 | 186.4% | 3.7% | 2.0% |
| 0.1 mM RS-105914-197 | 172.2% | 8.2% | 4.7% |
| 0.3 mM RS-105914-197 | 117.7% | 5.6% | 4.8% |
| 1.0 mM RS-105914-197 | 100.5% | 2.6% | 2.6% |

Example 5

Screening for Antagonists

Figure 7:
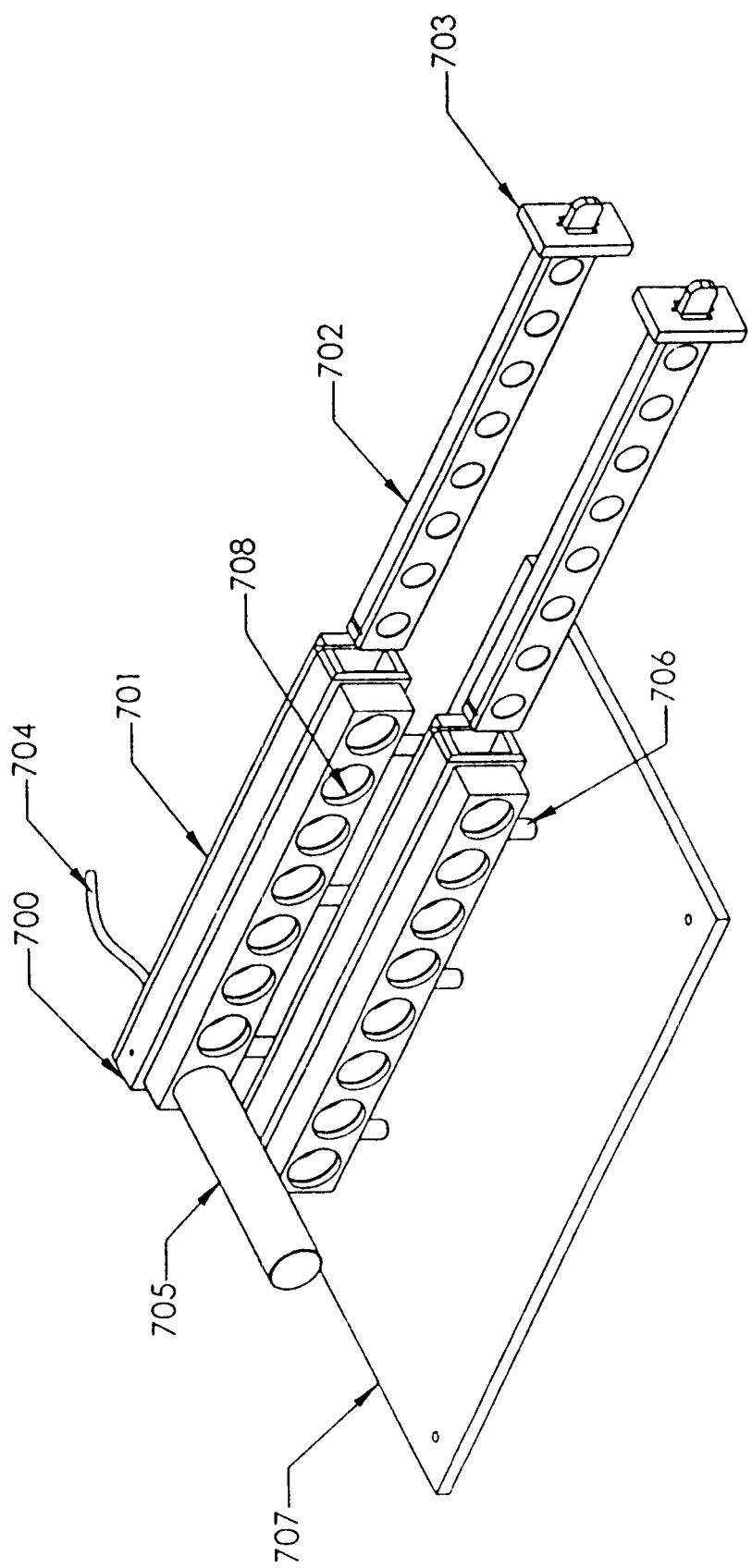
FIG. 7 shows a perspective view of one embodiment of a filter changer of the invention. The filter holder enclosure 700 & 701, filter holder support 702 & 703, trifurcated fiber optic assembly 704, photomultiplier (PMT) 705, support 706, holding platform 707, and light tight O-ring 708
Figure 9:
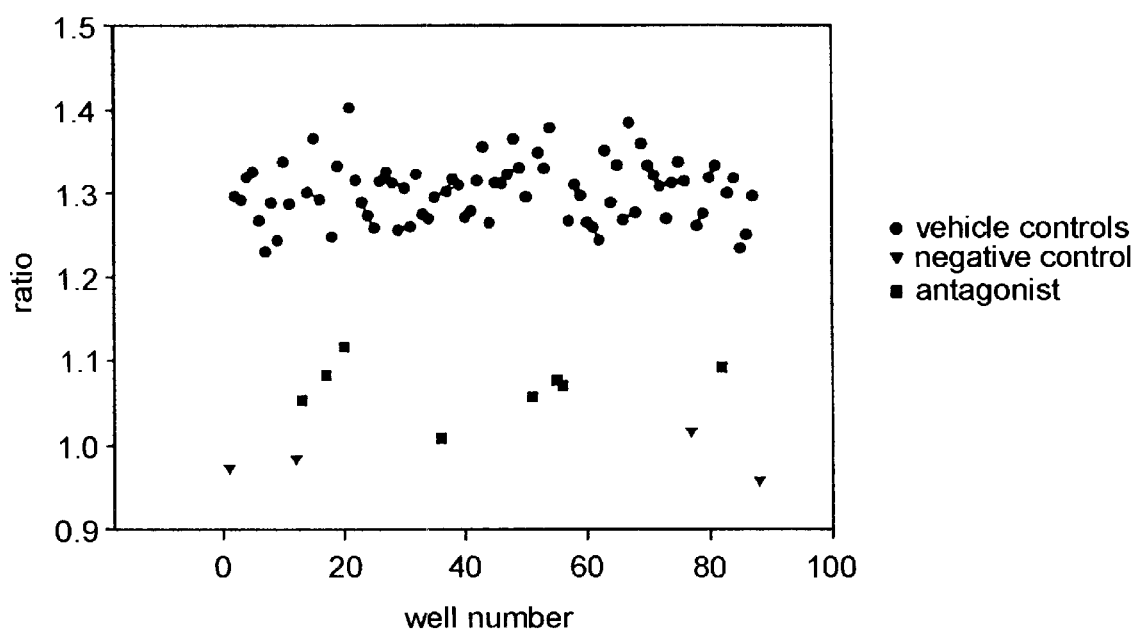
FIG. 9 shows the use of one embodiment of a device comprising the trifurcated ball lens assemblies of the invention to screen for ligand gated ion channel receptor antagonists.

To test whether it would be possible to identify antagonists on a single plate assay in a screening format, a protocol was set up. This protocol was designed such that compound additions were made from a chemical multiwell plate to the test plate, and the wells read continuously during compound addition FIG. 9 demonstrates the use of the device to identify antagonists in a screening mode. The results show ratio vs well number for the assay run in antagonist screening mode. End ratio values were averaged as in FIG. 9. A test antagonist (100 $\mu$M) was used to test screening sensitivity. Vehicle control wells had an equivalent final concentration of DMSO as the test antagonist treated wells. Negative controls received an addition of buffer instead of agonist. In this experiment, cells (HEK-293) were washed with assay buffer (160 mM NaCl, 10 mM HEPES, pH 7.4, 0.34 mM $Na_2HPO_4$, 0.4 mM $MgCl_2$, 0.5 mM $KH_2PO_4$, 5.37 mM KCl, 1.26 mM $CaCl_2$, 2 g/L D-glucose) and loaded with the fluorescent dyes CC2-DMPE and $DiSBAC_2$ as described in FIG. 7.

Publications

All publications, including patent documents and scientific articles, referred to in this application are incorporated by reference in their entirety for all purposes to the same extent as if each individual publication were individually incorporated by reference.

All headings are for the convenience of the reader and should not be used to limit the meaning of the text that follows the heading, unless so specified.

We claim:

1. A method of measuring at least two optical properties of emitted light from individual samples contained in a first plurality of addressable wells of a first multiwell plate, said method comprising:
    aligning the plurality of addressable wells with a plurality of ball lenses;
    dispensing reagent into said first plurality of addressable wells; and
    directing electromagnetic radiation through each of said ball lenses; and
    detecting substantially simultaneously the emission of light from said sample that is transmitted through said ball lenses at a first wavelength and at a second wavelength,
    wherein said first wavelength is different from said second wavelength;
    wherein said step of detecting is performed while dispensing the reagent into said first plurality of addressable wells.

2. The method of claim 1, wherein said electromagnetic radiation is directed to said plurality of ball lenses by a laser.

3. The method of claim 2, wherein said light emitted by said samples is focused by said plurality of ball lenses and is directed to at least one detector through at least one fiber optic bundle.

4. The method of claim 1 wherein said step of dispensing reagent comprises aspirating reagent from a second plurality of addressable wells of a second multiwell plate and dispensing the reagent into said first plurality of addressable wells.

5. A device, comprising:
    i) a liquid handler comprising at least one pipetting tip, said at least one pipetting tip comprising programmable control of aspiration from a first plurality of addressable wells of a first multiwell plate and programmable control of dispensation into a second plurality of addressable wells of a second multiwell plate,
    ii) an optical detector module comprising at least one detector, said at least one detector being in optical connection to said second plurality of addressable wells of said second multiwell plate and, said detector module simultaneously detecting at least two optical properties from each well of said second plurality of addressable wells of said second multiwell plate, iii) a plate handler to align said first multiwell plate and said second multiwell plate to said liquid handler, and said detector module, and to move said first multiwell plate and said second multiwell plate into and out of said device, and iv) a data processing and control module for coordinating the operation of said device, wherein said data processing and control module coordinates said plate handler to move said second plurality of addressable wells of said second multiwell plate to said liquid handler, and wherein, said data processing and control module collects data from said detector module wherein said device is adapted such that said liquid handler dispenses into said second plurality of addressable wells while said detector module is simultaneously detecting at least two optical properties from each well of said second plurality of addressable wells.

6. The device of claim 5, wherein said data processing and control module intermittently collects data from said detector module.

7. The device of claim 5, wherein said liquid handler dispenses into said second plurality of addressable wells of said second multiwell plate and there is a predefined delay before said detector module simultaneously detects at least two optical properties from each well of a plurality of said second plurality of addressable wells of said second multiwell plate.

8. The device of claim 5, wherein one of said two optical properties is light emission at a particular wavelength.

9. The device of claim 5, further comprising an optical irradiation module comprising at least one light source, wherein said at least one light source irradiates said second plurality of addressable wells of said multiwell plate.

10. The device of claim 9, wherein said at least one light source irradiates said second plurality of addressable wells of said multiwell plate intermittently.

11. The device of claim 10, wherein said detector module further comprises at least one trifurcated fiber optic bundle, said at least one trifurcated fiber optic bundle comprising at least one central optical fiber that is in direct optical communication with said at least one light source, and wherein said at least one central fiber optic bundle is coaxially aligned to at least one ball lens.

12. The device of claim 9, wherein, said at least one light source is programmably controlled to irradiate said second plurality of addressable wells of said multiwell plate at predefined times.

13. The device of claim 5, wherein said detector module further comprises at least one fiber optic bundle.

14. The device of claim 13, wherein said at least one fiber optic bundle comprises at least one trifurcated fiber optic bundle.

15. The device of claim 5, wherein said detector module further comprises at least one ball lens.

16. The device of claim 15, wherein said at least one ball lens is formed of a material selected from the group consisting of glass, fused silica, quartz and sapphire.

17. The device of claim 16, wherein said at least one ball lens further comprises an anti-reflective coating.

18. The device of claim 15, wherein said detector module further comprises at least one trifurcated fiber optic bundle, said at least one trifurcated fiber optic bundle having a diameter that is one third the diameter of said at least one ball lens.

19. A device, comprising:

i) an optical detector module comprising at least one fiber optic bundle comprising a trifurcated fiber optic bundle, at least one detector, said at least one detector being in optical connection to a plurality of addressable wells of a multiwell plate and, said detector module simultaneously detecting at any instant, at least two optical properties from each well of said plurality of addressable wells of said multiwell plate, ii) an optical irradiation module comprising at least one light source, wherein said at least one light source irradiates said plurality of addressable wells of said multiwell plate, iii) a plate handler to align said plurality of addressable wells of said multiwell plate to said detector module, and to move said multiwell plate into and out of said device, iv) an integration and control module for coordinating the operation of said device, v) a liquid handler for dispensing reagent into said plurality of addressable wells, wherein said integration and control module coordinates said plate handler to move said plurality of addressable wells of said multiwell plate to said detector module, wherein said detector module simultaneously detects at least two optical properties from each well of said plurality of addressable wells of said multiwell plate, wherein said data processing and control module collects data from said detector module, and wherein said device is adapted such that said liquid handler dispenses into said plurality of addressable wells while said detector module is simultaneously detecting at least two optical properties from each well of said plurality of addressable wells.

20. The device of claim 19, wherein said integration and control module intermittently collects data from said detector module.

21. The device of claim 19, wherein at least one of said two optical properties is light emission at a particular wavelength.

22. The device of claim 19, wherein said at least one light source irradiates said plurality of addressable wells of said multiwell plate intermittently.

23. The device of claim 19, wherein, said at least one light source is programmably controlled to irradiate said plurality of addressable wells of said multiwell plate at predefined times.

24. The device of claim 19, wherein said detector module further comprises at least one ball lens.

25. The device of claim 24, wherein said at least one ball lens is formed of a material selected from the group consisting of glass, fused silica, quartz and sapphire.

26. The device of claim 25, wherein said at least one ball lens further comprises an anti-reflective coating.

27. The device of claim 19, wherein said at least one trifurcated fiber optic bundle having a diameter that is one third the diameter of said at least one ball lens.

28. The device of claim 19, wherein said at least one trifurcated fiber optic bundle comprising a central optical fiber bundle that is in direct optical communication with said at least one light source, and wherein said central fiber optic bundle is coaxially aligned to said at least one ball lens.

29. The device of claim 19 further comprising at least one ball lens about three times larger in diameter than said addressable wells of said multiwell plate.

30. The device of claim 19 further comprising at least one ball lens about the same diameter as said addressable wells of said multiwell plate.

31. An optical detection system for detecting an optical attribute of a biological, biochemical or chemical sample, comprising:
   a) a light source that launches at least one predetermined wavelength of light,
   b) sample holder,
   c) a ball lens at a predetermined interrogation distance from said sample holder,
   d) a trifurcated fiber adapted for dual optical interrogation and in optical communication with said ball lens,
   e) a detector that detects light of at least one desired wavelength and in optical communication with said ball lens, and
   f) a reagent dispenser for dispensing reagent into said sample holder,
   wherein said optical detection system is adapted to detect light from a sample contained in said sample holder while said reagent dispenser is dispensing reagent is into said sample.

32. The optical detection system of claim 31, further comprising at least one positioner to controllably change said predetermined interrogation distance.

33. The optical detection system of claim 31, further comprising a liquid handling unit to dispense liquids into addressable wells.

34. The optical detection system of claim 31, further comprising a light activation system for triggering liquid handling unit to dispense liquids into addressable wells.

35. The optical detection system of claim 31, wherein said light source launches light through said trifurcated fiber to the location of at least one addressable well in a sample in said sample holder to monitor epifluorescence.

36. The optical detection system of claim 35, further comprising a computer control system to manage interrogation of a sample.

37. The optical detection system of claim 35, further comprising a sample transfer system to transfer at least one sample platform to said sample holder.

38. The optical detection system of claim 35, wherein said sample holder further comprises a positioning system.

39. The optical detection system of claim 31, wherein an object to be interrogated is generally at a focal plane of said ball lens.

40. A method of measuring at least two optical properties of emitted light from individual samples contained in a first plurality of addressable wells of a first multiwell plate, said method comprising:
   aligning the plurality of addressable wells with a plurality of ball lenses; directing electromagnetic radiation through each of said ball lenses, and detecting substantially simultaneously a first optical property and a second optical property of the emitted light from said samples that is transmitted through said ball lenses while dispensing reagent into said first plurality of addressable wells.

* * * * *